United States Patent [19]

Horodysky et al.

[11] 4,406,802

[45] Sep. 27, 1983

[54] FRICTION REDUCING ADDITIVES AND COMPOSITIONS THEREOF

[75] Inventors: Andrew G. Horodysky, Cherry Hill; Joan M. Kaminski, Clementon, both of N.J.

[73] Assignee: Mobil Oil Corporation, New York, N.Y.

[21] Appl. No.: 259,219

[22] Filed: Apr. 30, 1981

[51] Int. Cl.$^3$ .................. C10M 1/20; C10M 1/32; C10M 1/54
[52] U.S. Cl. .................. 252/49.6; 44/76; 252/389 R; 252/400 R
[58] Field of Search .............. 252/49.6, 389 R, 400 R; 44/76; 568/1

[56] References Cited

U.S. PATENT DOCUMENTS

| 3,009,791 | 11/1961 | Emrick | 44/76 X |
| 3,303,208 | 2/1967 | Liao | 44/76 X |
| 3,445,498 | 5/1969 | Cyba | 252/49.6 X |
| 3,505,226 | 4/1970 | Cyba | 252/49.6 |
| 3,533,945 | 10/1970 | Vogel | 252/49.6 |
| 3,544,614 | 12/1970 | Schwartz | 252/49.6 X |
| 3,560,386 | 2/1971 | Cyba | 252/49.6 |
| 4,022,713 | 5/1977 | Waldstein | 252/389 R |

*Primary Examiner*—W. J. Shine
*Attorney, Agent, or Firm*—Alexander J. McKillop; Michael G. Gilman; Howard M. Flournoy

[57] ABSTRACT

Mixed borated alcohol-amines, alcohol-amides, alcohol-ethoxylated amines, alcohol-ethoxylated amides, alcohol-hydroxyester, alcohol-imidazolines and alcohol-hydrolyzed imidazolines and mixtures thereof are effective multifunctional additives when incorporated into various organic media.

12 Claims, No Drawings

FRICTION REDUCING ADDITIVES AND COMPOSITIONS THEREOF

BACKGROUND OF THE INVENTION

1. Field of the Invention

This invention relates to lubricant additives and compositions thereof and, more particularly, to lubricant compositions comprising oils of lubricating viscosity or greases prepared therefrom containing a minor friction reducing amount of certain borated mixed alcohols, amides, amines and esters.

2. Description of the Prior Art

Many means have been employed to reduce overall friction in modern internal combustion engines, particularly automobile engines. The primary reasons are to reduce engine wear, thereby prolonging engine life and to reduce the amount of fuel consumed by the engine.

Many of the solutions to reducing fuel consumption have been strictly mechanical, as for example, setting the engines for a leaner burn or building smaller cars and smaller engines. However, considerable work has been done with lubricants, mineral and synthetic, to enhance their friction properties by modifying them with friction reducing additives.

Certain alcohols, mixtures of alcohols and other organic compounds have been used as intermediates in the manufacture of a variety of lubricant additives. However, the use of alcohols themselves, for example, has not been widespread as engine oil additives because of potential oxidative and thermal instability and volatility difficulties. It has now been found that certain borated mixed alcohols, amides, amines and hydroxy esters provide friction reducing characteristics that non-borated compositions lack; in addition, the borated mixed derivatives improve oxidative and thermal stability, volatility and bearing corrosion inhibiting properties. These borated mixed compositions are, to the best of applicants' knowledge, novel and have not been used as friction reducing or multifunctional additives suitable for use in lubricating compositions and in fuels such as in gasoline, diesel fuel, jet fuel, etc. to improve fuel economy. The subject mixed borated compositions perform better than mixtures of individual borated materials, e.g., borated mixed oleyl amine and oleyl alcohol outperforms a mixture of borated oleyl alcohol and borated oleyl amine.

SUMMARY OF THE INVENTION

This invention is directed to novel additive compounds, i.e., borates of mixed alcohols, amides, amines, and hydroxy esters, ethoxylated amines, and ethoxylated amides and mixtures thereof such as mixed alcohol, amine borates, mixed alcohol, and ethoxylated amine borates. In addition to these novel compounds the invention is also directed to lubricant compositions having reduced friction containing such compounds and to a method of reducing fuel consumption in internal combustion engines by treating the moving surfaces thereof with said compositions. Further, as noted hereinabove the novel compounds referred to also possess significant antioxidant characteristics and bearing corrosion inhibiting properties.

DESCRIPTION OF SPECIFIC EMBODIMENTS

The generalized structure of the alcohols before boration is:

ROH where R may contain any desirable number of carbon atoms based on such factors as oil solubility; however, R usually will contain from about 10 to about 30 carbon atoms and is an alkyl or substituted alkyl group which may be primary, secondary or tertiary, straight-chain, branched or cyclic, it may contain one or more double bonds, halogen or one or more sulfur atoms or an aromatic ring. Examples include such as decyl alcohol, dodecyl alcohol, oleyl alcohol, stearyl alcohol, p-nitrobenzyl alcohol, ethyl-octyl alcohol and mixed $C_{12}$–$C_{15}$ linear alkanols. Alcohols having from about 12 to 24 carbon atoms are particularly useful. Particularly preferred are $C_{10}$–$C_{15}$ linear alkanols and $C_{10}$–$C_{12}$ branched alkanols such as 2-ethyl-octanol and $C_{15+}$ alcohols such as oleyl alcohol and stearyl alcohol.

The generalized structure of the hydroxyalkyl or hydroxyalkenyl hydrocarbyl amides useful herein is:

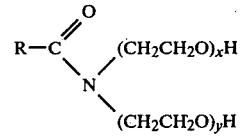

where R is as described above. Examples include bis(2-hydroxyethyl) oleamide, bis(2-hydroxyethyl) cocoamide, bis(2-hydroxyethyl) soyamide, bis(2-hydroxyethyl) octadecylamide, polyoxyethylene (5) oleamide, polyoxyethylene (4) cocoamide, polyoxyethylene (5) soyamide, etc. x and y may be the same or different and each is from 1 to about 10, however, the sum of x and y must always be 2 or greater. Propoxylated amides could also be used.

The generalized structure of the amines before boration is:

where R is as described above. Both saturated and unsaturated amines can be used; diamines and polyamines are also useful. Examples include stearyl amine, cocoamine, laurylamine, soyamine, N-oleyl 1,3-propylenediamine, oleyl amine, aniline and dinitrophenylamine. R as stated hereinabove with respect to both the amides and the amines disclosed herein is as defined herein above.

The generalized structure of the hydroxyalkyl or hydroxyalkenyl hydrocarbyl amines suitable for use in the present invention is:

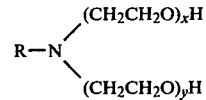

and as stated hereinabove x and y may be the same or different and each is from 1 to about 10 and the sum of x and y must be 2 or greater.

Examples are bis(2-hydroxyethyl) oleylamine, bis(2-hydroxyethyl) soyamine, bis(2-hydroxyethyl) cocoamine, bis(2-hydroxyethyl) octadecylamine, polyoxyethylene (5) oleylamine, polyoxyethylene (5) soyaamine, polyoxyethylene (4) cocoamine, etc.

The generalized structure of the hydroxyesters are exemplified by the following general structure:

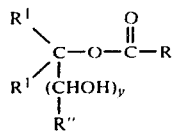

where R is a hydrocarbyl group having from about 10 to about 30 carbon atoms; said hydrocarbyl moiety may be alkyl, straight or branched, cyclic or substituted and may contain one or more double bonds, halogen or one or more sulfur atoms or aromatics rings; $R^1 = CH_2OH$, $CH_3$ or H; $R'' = CH_2OH$ or H and y is from 1 to about 5. The hydroxy esters may be made by the reaction of polyhydroxy alcohols with organic acids. For example, glycerol and oleic acid are used in the preparation of glycerol monooleate. Thioglycerol hydroxyesters can also be used.

The hydroxy esters must contain at least one free hydroxyl group but may contain two or more. The hydroxy esters may also contain one ester group (as in glycerol monooleate) or more (as in glycerol dioleate). The esters can be used in pure form, or preferably in mixtures such as mixtures of glycerol mono- and dioleate.

Sorbitan hydroxyesters and hydroyesters prepared from trimethylolpropane and pentaerythritol are also useful, e.g., sorbitan monooleate, trimethylolpropane monooleate, trimethylolpropane dioleate, pentaerythritol dioleate monolaurate and the like.

Also useful are hydroxyalkyl or hydroxyalkenyl alkyl or alkenylimidazolines and/or hydrolysis products of the imidazoline. The general structure of such compounds can be as described below:

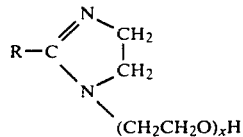

where R has from about 10-30 carbon atoms and may be alkyl or alkenyl, arylalkyl, alkyl aryl, etc. and x is from 1 to about 5. Their respective ring-opened hydrolysis products are made by treatment of the above-described imidazolines with at least molar amounts of water.

The borated derivatives can be conveniently produced by the reaction of selected mixtures of the compounds in accordance herewith with boric acid in a suitable solvent or solvents at temperatures ranging from about 110° C. to about 280° C. Specific reaction conditions and molar equivalents vary with the reactants and can be readily determined by one of ordinary skill in the art. Besides direct treatment with boric acid several other boration procedures which are well known in the art can be used, e.g., transesterification with a trialkyl borate such as tributyl borate. In any event the boration procedure is most conveniently a one-pot, one-step process.

The borated mixed materials are much more effective friction reducers than their non-borated counterparts or physical mixtures of the individual borated materials. As noted above the borated mixed materials also possess antioxidant and corrosion inhibiting properties not generally found in the non-mixed borated materials and to an even greater degree than the individual borated materials. That is, the borated mixed materials perform in a far superior manner to an equivalent physical mixture of each specific borated material. Further, the higher molecular weight borates have increased resistant to hydrolysis and retain their friction reducing characteristics even in the presence of water at elevated temperatures.

Exemplary mixed borates so prepared are mixed alcohol-amine borates such as:

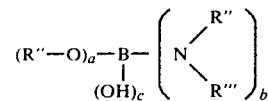

where a and b=1 or 2 c=0, or 1, R'' and R''' have from about 10 to about 24 carbon atoms or can be H.

The structure of mixed alcohol-ethoxylated amide borates can be generalized as follows:

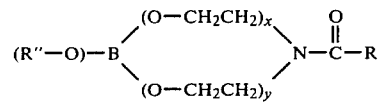

and various similar or related ring-opened borate structures where R, R'', x, y are as defined above or mixed alcohol-ethoxylated amines borates such as:

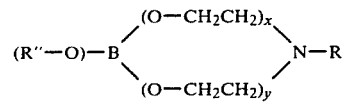

and various ring-opened structures where x, y, R and R'' are as defined above.

The structure of mixed alcohol-hydroxyester borates can have the general structures:

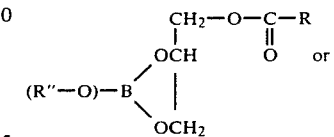

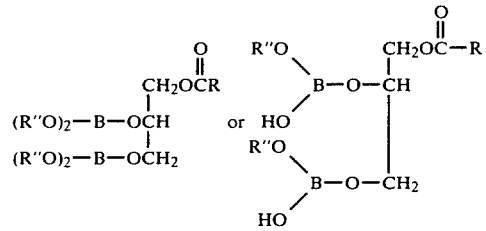

For example, mixed borate trimethylolpropane hydroxyesters have the following generalized structures:

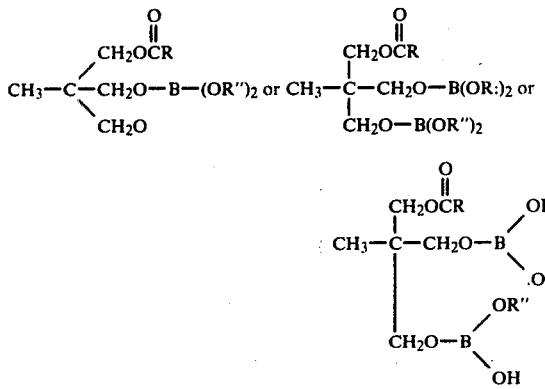

Also included in the present invention are mixed alcohols and imidazoline borates and mixed alcohol-hydrolyzed imidazoline borates.

The amount of these novel additives required to be effective in lubricant compositions ranges from about 0.1 to about 10% by weight of the total lubricant composition. Preferred is from about 0.5 to 5 wt. %. The additives of this invention may also be used in combination with other systems having additives in conventional amounts for their known purpose. The use of additive concentrations of these borated materials in premium quality automotive and industrial lubricants further improves upon such fluids' fuel economy characteristics. The non-metallic compositions described herein are useful, therefore, at moderate concentrations and do not contain any potentially undesirable phosphorus, corrosive sulfur or metallic salts.

The lubricants contemplated for use herein include both mineral and synthetic hydrocarbon oils of lubricating viscosity, mixtures of mineral and synthetic oils, and greases prepared therefrom. The synthetic hydrocarbon oils include long chain alkanes such as cetanes and olefin polymers such as trimers and tetramers of octene and decene. These synthetic oils can be mixed with other synthetic oils which include (1) ester oils such as pentaerythritol esters of monocarboxylic acids having 2 to 20 carbon atoms, (2) polyglycol ethers, (3) polyacetals and (4) siloxane fluids. Especially useful among the synthetic esters are those made from polycarboxylic acids and monohydric alcohols. More preferred are the ester fluids made from pentaerythritol, and an aliphatic monocarboxylic acid containing from 1 to 20 carbon atoms, or mixtures of such acids.

Lubricant compositions containing the novel friction reducing additives of the present invention can also include additive concentations of ashless dispersants, detergents, inhibitors, antiwear, extreme pressure, antifoam and viscosity improving additives and the like without significantly affecting the performance of the additives in accordance with the invention. The novel friction reducers can also be advantageously used in internal combustion engine fuels, effective friction reducing amounts vary, from about 2 to about 1000 lbs. per thousand barrels of fuel and preferably from about 50 to about 300 lbs. per thousand depending, inter alia, on the specifications of the particular fuel.

Having described the invention in general terms, the following are offered as specific illustrations thereof.

Oleyl alcohol, oleyl amine, 1-(2-hydroxyethyl)-2-heptadecenyl imidazoline, $C_{12}$-$C_{15}$ alkanols, bis(2-hydroxyethyl) oleamide, bis(2-hydroxyethyl) oleamine, and glycerol monooleate used in the examples set out below were obtained commercially.

EXAMPLE 1

Borated Mixed Oleyl Alcohol and Oleyl Amine

Approximated 134 g of oleyl alcohol and 133 g of oleyl amine were charged to a reactor equipped with a thermometer, an overhead stirrer, and a Barrett trap and condenser for azeotropic distillation. Approximately 111 g of n-butanol and 20.6 g boric acid were also charged to said reactor. The reaction solution was heated to 110° C. at which time water began to distill over. In 5 hours 16.8 cc $H_2O$ were removed as the reaction temperature increased to 160° C. The solvent was removed by vacuum distillation, and the borated product was filtered over diatomaceous earth to yield a clear, brown fluid.

EXAMPLE 2

Ring-Opening Hydrolysis of 1-(2-Hydroxyethyl)-2-Heptadecenylimidazoline

A mixture of 1-(2-hydroxyethyl)-2-heptadecenylimidazoline (40 g), water (9.4 g), and ethanol (9.6 g) was stirred and heated at 90° C. for 3 hours. The water and ethanol were removed by high speed rotary evaporation, and the resulting product was a golden waxy solid. The infrared spectrum of the product contained a strong carbonyl absorption band in the 1640-1650 $cm^{-1}$ region and showed no characteristic imidazoline carbon-nitrogen imido band at 1600 $cm^{-1}$, thereby, indicating complete ring-opening of the starting imidazoline.

EXAMPLE 3

Borated Mixed $C_{12}$-$C_{15}$Alkanols and Hydrolyzed 1-(2-Hydroxyethyl)-2-Heptadecenylimidazoline Approximately 103 g of $C_{12}$-$C_{15}$ alkanols and 184 g of hydrolyzed 1-(2-hydroxyethyl)-2-heptadecenylimidazoline (hydrolyzed as described in Example 2) were charged to a reactor equipped with a thermometer, an overhead stirrer, and a Barrett trap and condenser for azeotropic distillation. Approximately 111 g n-butanol and 31 g boric acid were also charged to said reactor. The reaction solution was heated to 110° C. at which time water began to distill over. In 5 hours 15 cc $H_2O$ were removed as the reaction temperature increased to 163° C. The solvent was removed by vacuum distillation, and the borated product was filtered over diatomaceous earth to yield a clear, brown fluid.

EXAMPLE 4

Borated Mixed Oleyl Alcohol and Bis(2-hydroxyethyl) Oleamide

Approximately 36 g bis(2-hydroxyethyl) oleamide (made by the reaction of oleic acid and diethanolamine) and 53 g oleyl alcohol were charged to a 500 Ml glass reactor fitted with an agitator, Dean-Stark tube and nitrogen sparge to exclude air. Approximately 10 g boric acid and 60 g toluene solvent were added. The reactants were heated to 195° C. over a period of 4 hours during which time 8½ g water were removed by azeotropic distillation. The solvent was removed by vacuum distillation. The borated product was filtered over diatomaceous earth to yield a clear, orange fluid.

EXAMPLE 5

Borated Mixed Oleyl Alcohol and Glycerol Monooleate

Approximately 165 g glycerol monooleate (60/40 mixture glycerol monooleate/glycerol dioleate) and 134 g oleyl alcohol were charged to a one liter glass reactor equipped as in Example 4. Approximately 25 g boric acid and 50 g toluene solvent were added. The reactants were heated up to 200° C. over a period of 6 hours after which time water evolution via azeotropic distillation ceased. The solvent was removed by vacuum distillation and the borated product was filtered over diatomaceous earth to yield a clear, amber fluid.

EXAMPLE 6

Borated Mixed Alcohols and Ethoxylated Amines

Approximately 1450 grams of oleyl alcohol, 1900 grams of bis(2-hydroxyethyl) oleylamine, 410 grams of boric acid, 40 grams of butanol and 200 grams of toluene were charged to a 5 liter reactor equipped with an agitator and Dean-Stark tube. After a 7 hour reaction period at temperatures up to 170° C., water evolution terminated. Approximately 73· grams of mixed linear alkanols, obtained commercially and having an average molecular weight of 208 and an hydroxyl number of 270 (approximately 80% of the alcohols were linear alcohols with the following carbon number distribution: 17.7% $C_{12}$, 30% $C_{13}$, 28% $C_{14}$ and 24% $C_{15}$) were added, and the mixture heated at 170° for an additional hour. The solvents were removed by vacuum distillation and the crude product filtered over diatomaceous earth to yield an orange fluid.

Certain of the borated materials were then dissolved in a SAE5W-20, automotive engine oil containing a standard additive package as described above and then subjected to testing in the Low Velocity Friction Apparatus Test described below. Test results are reported in Table 1, below.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulted by air pressure on the bottom of the piston. The drive system consists of an infinitely variable-speed hydraulic transmission driven by a ½ HP electric motor. To vary the sliding speed, the output speed of the transmission is regulated by a lever cam-motor arrangement.

Procedure

The rubbing surfaces and 12-13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25-195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

Thus, the data are expressed in this form in the Table below.

TABLE 1

| FRICTION CHARACTERISTICS | | | |
|---|---|---|---|
| | Additive Conc., | Reduction or % Change in Coefficient of Friction | |
| Example No. | Wt. % | 5 ft./min. | 30 ft./min. |
| Base Oil SAE 5W-20 | 0 | — | — |
| Example 1: | | | |
| Borated mixed oleyl alcohol and oleyl amine | 4 | 43 | 31 |
| Example 3: | | | |
| Borated mixed $C_{12}$-$C_{15}$ alkanols and hydrolyzed 1-(2-hydroxyethyl) 2-heptadecenylimidazoline | 4 | 35 | 30 |
| Example 4: | | | |
| Borated mixed oleyl alcohol and bis(2-hydroxyethyl) oleamide | 4 | 30 | 25 |
| Example 5: | | | |
| Borated mixed oleyl alcohol and glycerol monooleate | 4 | 35 | 22 |
| Example 6: | | | |
| Borated mixed oleyl alcohol, mixed $C_{12}$-$C_{15}$ alkanols and bis(2-hydroxyethyl) oleylamine | 4 | 32 | 22 |
| | 2 | 36 | 28 |
| | 1 | 31 | 24 |

Bearing corrosion inhibiting properties of representative compounds were tested via copper corrosivity tests, ASTM D 130-6, ASTM D 130-9. The results are reported in Table 2, below.

TABLE 2

| COPPER STRIP CORROSIVITY CHARACTERISTICS | | | |
|---|---|---|---|
| Example No. | Concentration in 200° SPN | ASTM D 130-6 250° F., 3 hrs. | ASTM D-130-9 210° F., 6 hrs. |
| Example 1: | | | |
| Borated mixed oleyl alcohol and oleyl amine | 3 | 1A | 1B |
| | 1 | 1A | 1B |
| Example 3: | | | |
| Borated mixed $C_{12}$-$C_{15}$ alkanols and hydrolyzed 1-(2-hydroxyethyl)-2-heptadecenyl-imidazoline | 3 | 1A | 1A |
| | 1 | 1A | 1A |
| Example 4: | | | |
| Borated mixed oleyl alcohol and bis(2-hydroxyethyl) oleamide | 3 | 1A | 1A |
| | 1 | 1B | 1A |

TABLE 2-continued

| | COPPER STRIP CORROSIVITY CHARACTERISTICS | | |
|---|---|---|---|
| Example No. | Concentration in 200" SPN | ASTM D 130-6 250° F., 3 hrs. | ASTM D-130-9 210° F., 6 hrs. |
| Example 5: | | | |
| Borated mixed oleyl alcohol and glycerol monooleate | 3 1 | 1A 1A | 1A 1A |
| Example 6: | | | |
| Borated mixed oleyl alcohol, mixed $C_{12}$-$C_{15}$ alkanols and bis(2-hydroxyethyl) oleylamine | 3 1 | 1A 1A | 1A 1A |

Certain of the examples were also tested for their antioxidation characteristics in the B-10 Catalytic Oxidation Test at 325° F. for 40 hours. The test lubricant composition is subjected to a stream of air which is bubbled through the composition at a rate of 5 liters per hour at 450° F. for 24 hours. Present in the composition comprising a 200 seconds paraffinic neutral oil in addition to the additive compound were metals commonly used as materials to construct engines namely:

(a) 15.6 sq. in. of sand-blasted iron wire;
(b) 0.78 sq. in. of polished copper wire;
(c) 0.87 sq. in. of polished aluminum wire; and
(d) 0.107 sq. in. of polished lead surface.

The test results are reported below in Table 3.

TABLE 3

| | CATALYTIC OXIDATION TEST 40 hours at 325° F. | | | |
|---|---|---|---|---|
| Example No. | Additive conc., wt. % | Lead Loss, mg. | % Increase in Viscosity of Oxidized Oil Using KV @ 100° C. | Neut. Number |
| Base oil 200" paraffinic neutral lubrication oil | — | 1.2 | 67 | 3.62 |
| Example 1: | | | | |
| Borated mixed oleyl alcohol and oleyl amine | 3 1 | 0.0 0.0 | 32 14 | 2.47 3.48 |
| Example 3: | | | | |
| Borated mixed $C_{12}$-$C_{15}$ alkanols and hydrolyzed 1-(2-hydroxyethyl)-2-heptadecenyl imidazoline | 3 1 | 4.6 0.0 | 15 14 | 2.27 2.21 |
| Example 4: | | | | |
| Borated mixed oleyl alcohol and bis(2-hydroxyethyl) oleamide | 3 1 | 0.0 1.0 | 20 17 | 2.55 2.68 |
| Example 5: | | | | |
| Borated mixed oleyl alcohol and glycerol monooleate | 3 1 | 0.0 0.0 | 32 21 | 2.40 1.83 |
| Example 6: | | | | |

TABLE 3-continued

| | CATALYTIC OXIDATION TEST 40 hours at 325° F. | | | |
|---|---|---|---|---|
| Example No. | Additive conc., wt. % | Lead Loss, mg. | % Increase in Viscosity of Oxidized Oil Using KV @ 100° C. | Neut. Number |
| Borated mixed oleyl alcohol, mixed $C_{12}$-$C_{15}$ alkanols and bis(2-hydroxyethyl) oleylamine | 3 1 | 0.0 0.0 | 15 13 | 1.96 1.43 |

It can be clearly seen that these mixed borates impart significant friction reducing, corrosion inhibiting, and antioxidant characteristics to oleagenous lubricant compositions.

It is understood by one of ordinary skill in the art that modifications and variations from the exemplary material disclosed herein can be readily made and is within the scope of this specification.

We claim:

1. A lubricant composition comprising a major proportion of an oil of lubricating viscosity or grease prepared therefrom and a minor effective amount of a multi-functional additive compound having friction reducing and oxidation and corrosion inhibiting characteristics selected from the group consisting of borated mixed $C_{12}$-$C_{15}$ alcohols and hydrolyzed 1-(2-hydroxyethyl)-2-heptadecenylimidazoline; and borated mixed oleyl alcohol and glycerol monooleate or mixtures of said borated compounds prepared by borating under suitable boration conditions selected mixtures of appropriate compounds in suitable solvent or mixtures thereof at temperatures of from about 110° to 280° C. said compounds having one or more alkyl or substituted alkyl groups attached thereto, and where said group is straight or branched chain, cyclic or contains one or more double bonds, halogen or one or more sulfur atoms or aromatic rings and said group having from about 10 to about 30 carbon atoms.

2. The composition of claim 1 wherein the additive is borated mixed $C_{12}$-$C_{15}$ alcohols and hydrolyzed 1-(2-hydroxyethyl)-2-heptadecenylimidazoline.

3. The composition of claim 1 wherein the additive is borated mixed oleyl alcohol and glycerol monooleate.

4. The composition of claim 1 wherein said oil is selected from mineral oils, synthetic oils and mixtures thereof.

5. The composition of claim 1 wherein said oil is a mineral oil.

6. The composition of claim 1 wherein said oil is a synthetic oil.

7. The composition of claim 1 wherein said oil is a mixture of synthetic oils and/or mineral oils.

8. The composition of claim 1 wherein said major proportion comprises a grease.

9. A borated additive as described in claim 2.

10. A borated additive as described in claim 3.

11. The composition of claim 1 wherein said boration is via boric acid.

12. The composition of claim 1 wherein the said boration is via transesterification with a trialkyl borate.

* * * * *